(12) United States Patent
Seo et al.

(10) Patent No.: US 7,655,735 B2
(45) Date of Patent: Feb. 2, 2010

(54) BIODEGRADABLE MULTI-BLOCK POLYMERIC COMPOSITION CAPABLE OF SOL-GEL TRANSITION AND PHARMACEUTICAL COMPOSITION COMPRISING THE SAME

(75) Inventors: Min-Hyo Seo, Daejeon (KR); Bong-Oh Kim, Daejeon (KR); Myung-Seob Shim, Seoul (KR); Sang-Jun Lee, Daejeon (KR)

(73) Assignee: Samyang Corporation, Seoul (KR)

( * ) Notice: Subject to any disclaimer, the term of this patent is extended or adjusted under 35 U.S.C. 154(b) by 316 days.

(21) Appl. No.: 10/546,431

(22) PCT Filed: Aug. 1, 2005

(86) PCT No.: PCT/KR2005/002511

§ 371 (c)(1),
(2), (4) Date: Feb. 28, 2007

(87) PCT Pub. No.: WO2005/014067

PCT Pub. Date: Sep. 2, 2006

(65) Prior Publication Data

US 2007/0161753 A1 Jul. 12, 2007

(30) Foreign Application Priority Data

Aug. 2, 2004 (KR) .................... 10-2004-0060757

(51) Int. Cl.
*C08G 63/16* (2006.01)
*C08G 63/676* (2006.01)
*C08G 65/332* (2006.01)

(52) U.S. Cl. .................... 525/403; 525/408; 514/772.7; 424/94.1; 424/280.1

(58) Field of Classification Search ................ 525/403, 525/408, 409; 514/772.7; 424/94.1, 280.1
See application file for complete search history.

(56) References Cited

U.S. PATENT DOCUMENTS

| 5,364,908 A | 11/1994 | Oishi et al. |
| 6,083,524 A | 7/2000 | Sawhney et al. |
| 2003/0187148 A1 | 10/2003 | Cohn et al. |

FOREIGN PATENT DOCUMENTS

| EP | 1382628 A1 | 1/2004 |
| WO | WO-2004022121 A1 * | 3/2004 |

* cited by examiner

*Primary Examiner*—Irina S Zemel
*Assistant Examiner*—Jeffrey Lenihan
(74) *Attorney, Agent, or Firm*—Fulbright & Jaworski LLP

(57) ABSTRACT

The present invention relates to an ionic multi-block copolymer composition comprising tri-block copolymers having a polypropyleneoxide or polybutyleneoxide block positioned between two polyethyleneoxide blocks and the tri-block copolymers are connected through dicarboxylic acid linkages forming a multi-block copolymer having a weight average molecular weight of more than 40,000 Dalton. The higher weight average molecular weight enables the hydrolgel formed from the multi-block copolymer of the present invention to maintain its gel status for more than several days.

27 Claims, 10 Drawing Sheets

BIODEGRADABLE MULTI-BLOCK POLYMERIC COMPOSITION CAPABLE OF SOL-GEL TRANSITION AND PHARMACEUTICAL COMPOSITION COMPRISING THE SAME

CROSS REFERENCE TO RELATED APPLICATION

This application claims priority to and the benefit of Korean Patent Application No. 2004-0060757 filed on Aug. 2, 2004, which is hereby incorporated by reference for all purposes as is fully set forth herein.

BACKGROUND OF THE INVENTION

1. Field of the Invention

The present invention relates to a biodegradable multi-block copolymer having an improved release profile and control of the release rate for various drugs. Particularly, the present invention provides a multi-block copolymer comprising ABA-type tri-block copolymers wherein the A block is polyethyleneoxide and the B-block is a polypropyleneoxide or polybutyleneoxide block, and wherein the resulting PEO-PPO (or PBO)-PEO blocks are connected through dicarboxylic linkages which can be hydrolyzed in the living body.

2. Description of the Related Art

Hydrogels have biocompatible properties and thus have been widely used as drug carriers. A therapeutic agent is entrapped within the crosslinked hydrogel matrix and upon release passes through interstices in the matrix.

Early drug delivery systems used gels having thermoplastic properties. The thermoplastic system involved the formation of a polymeric solution in solvents. Before injection into the body, a drug was added to the polymeric solution. After injection the polymeric solution quickly formed a gel by exposure to body fluids. However, the early drug delivery systems had problems in that they could be toxic and irritating to the body due to the presence of the organic solvent.

Recently, a gel drug delivery system using aqueous solutions has been developed. The system uses a block copolymer which is composed of polyethylene oxide and polypropylene oxide. The polyethylene oxide and polypropylene oxide copolymers, when at sufficient concentration and temperature, absorb water to form a gel (U.S. Pat. Nos. 4,188,373, 4,478,822 and 4,474,751). An example of the polymeric solution is known as a poloxamer and is commercially available. The poloxamer is a tri-block copolymer of PEO-PPO-PEO wherein PEO is a polyethylene oxide block and PPO is a polypropylene oxide block (PPO). The poloxamer has a molecular weight ranging from 9,840 to 14,600 Daltons. However, the poloxamer-based gel is non-biodegradable. In order to undergo phase transition under physiological conditions, a poloxamer polymer solution having a concentration of more than 18 to 20% is necessary. However, such a concentrated solution has a very high viscosity in the liquid phase and thereby may induce unfavorable reactions in the living body. Although when injected into a living body, it is quickly transformed into a gel, the gel status can only be maintained for several hours and therefore it has limited application as a drug delivery system.

In order to solve these problems, Sosnik et al. synthesized the compound of formula 1, wherein poloxamer 407 blocks are connected by a urethane linkage by reacting poloxamer 407 and hexamethylene diisocyanate (Winter Symposium & 11$^{th}$ International Symposium on Recent Advances in Drug Delivery Systems, 2003 Controlled Release Society, #117)).

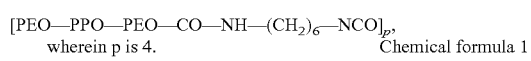
wherein p is 4.    Chemical formula 1

It is disclosed in Sosnik that the compound with the chemical formula 1 has a viscosity several times higher than poloxamer 407 in the case of a 17% aqueous solution and a significantly longer time in maintaining its gel status at high temperatures. However, there are problems with the polymer in that it is non-biodegradable and has a molecular weight of more than 50,000 Daltons and thus excretion from the body is difficult.

X. Zhao et al. discloses a biodegradable polymeric composition including the poloxamer 407 of chemical formula 2 (30$^{th}$ annual meeting and exhibition of the controlled release society, Glasgow, Scotland, Jul. 19-23, 2003). In preparation of the polymer, a poloxamer 407 is reacted with disuccincimidyl carbonate (DSC), so that poloxamer 407 blocks are connected through carbonate linkages as shown in Chemical Formula 2.

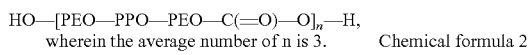
wherein the average number of n is 3.    Chemical formula 2

U.S. Patent Application No. 20030187148 discloses a polymeric composition wherein poly(hydroxyl carboxylic acid) blocks are introduced into both terminal ends of poloxamer 407 and the resulting penta-blocks are chain-extended through a HDI (hexamethylene diisocyanate) linker. However, the polymer is non-biodegradable because urethane linkages are non-biodegradable.

U.S. Pat. No. 6,348,558 discloses a biodegradable polymer wherein at least two polyalkylene oxide oligomers are connected through hydrolytic carbonate linkers.

However, the above disclosed polymers only have hydroxyl groups at the terminal ends and the release rate of a drug from the gel depends only on the diffusion rate which is determined by the viscosity of the gel. Thus it is impossible to control the release rate of the drug.

Therefore, there is a need for a biodegradable polymeric composition which has low toxicity and an improved release profile, and can control of the release rate of various drugs.

SUMMARY OF THE INVENTION

The present invention provides a multi-block copolymer comprising ABA-type tri-block copolymers wherein the A block is a polyethyleneoxide block and the B-block is a polypropyleneoxide or polybutyleneoxide block, and wherein the resulting PEO-PPO (or PBO)-PEO blocks are connected through biodegradable dicarboxylic linkages.

The present invention also provides a pharmaceutical composition including the multi-block copolymer of the present invention.

The present invention also provides methods of making and using the multi-block copolymer of the present invention.

The multi-block copolymer composition of the present invention can improve gel maintenance in an aqueous solution by increasing the molecular weight of the copolymer through formation of multiple blocks of PEO-PPO (or PBO)-PEO units. The multi-block copolymer can be applied for use as a sustained release drug delivery system for various drugs.

Additional features and advantages of the invention will be apparent from the detailed description that follows, which when taken in conjunction with the accompanying drawings together illustrate, by way of example, features of the invention.

DETAILED DESCRIPTION OF THE ILLUSTRATED EMBODIMENTS

Figure 1:
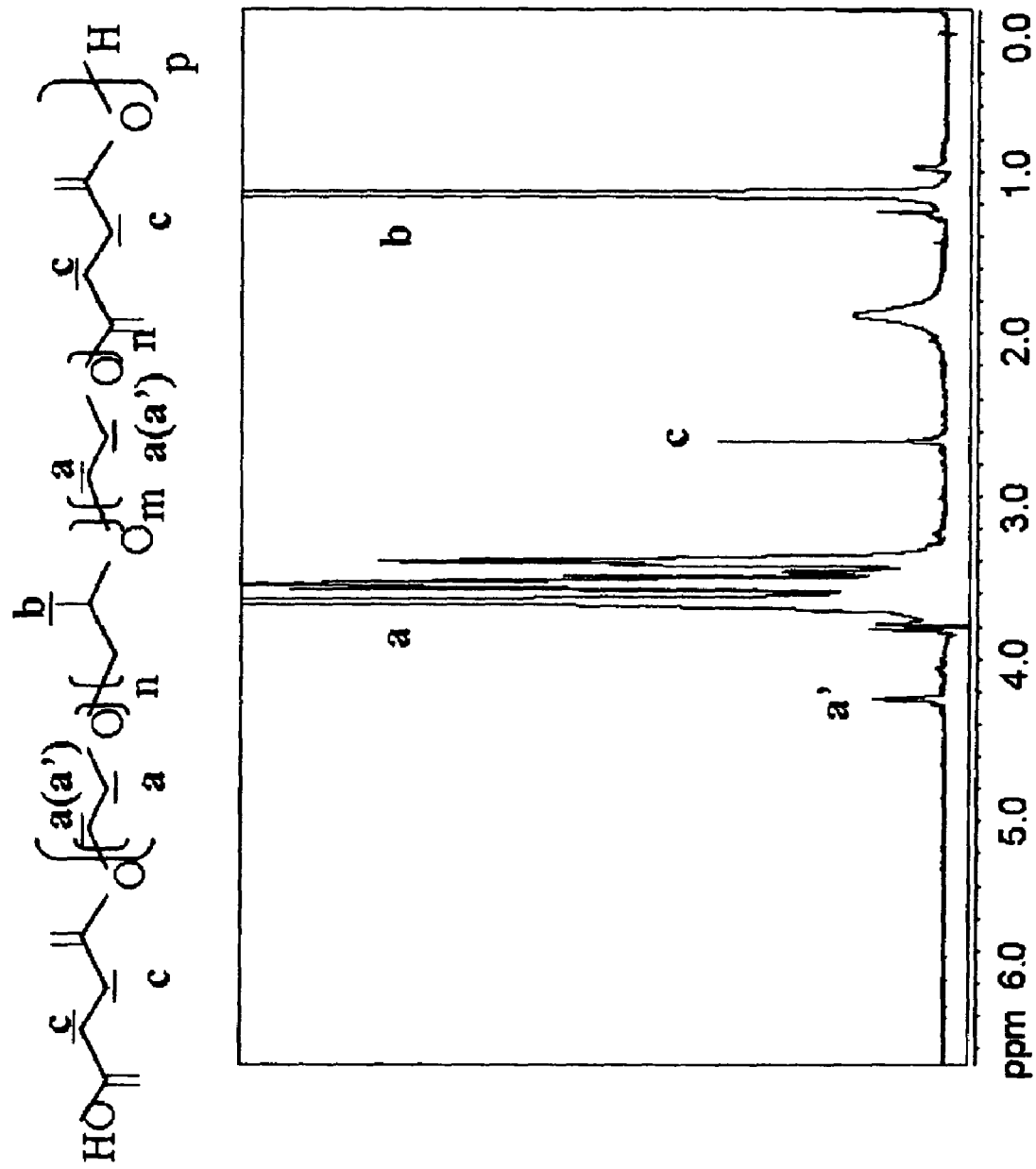
FIG. 1 is a $^1$H-NMR spectrum of a multi-block poloxamer according to Example 1.

Before the present polymeric compositions and methods of using and making thereof are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a polymer containing "a terminal group" includes reference to two or more such groups, and reference to "a hydrophobic drug" includes reference to two or more of such drugs.

In describing and claiming the present invention, the following terminology will be used in accordance with the definitions set out below.

As used herein, the term "bioactive agent" or "drug" or any other similar term means any chemical or biological material or compound suitable for administration by methods previously known in the art and/or by the methods taught in the present invention and that induce a desired biological or pharmacological effect. Such effects may include but are not limited to (1) having a prophylactic effect on the organism and preventing an undesired biological effect such as preventing an infection, (2) alleviating a condition caused by a disease, for example, alleviating pain or inflammation caused as a result of disease, and/or (3) either alleviating, reducing, or completely eliminating a disease from the organism. The effect may be local, such as providing for a local anesthetic effect, or it may be systemic.

As used herein, the term "biodegradable" or "biodegradation" is defined as the conversion of materials into less complex intermediates or end products by solubilization hydrolysis, or by the action of biologically formed entities which can be enzymes or other products of the organism.

As used herein, the term "biocompatible" means materials or the intermediates or end products of materials formed by solubilization hydrolysis, or by the action of biologically formed entities which can be enzymes or other products of the organism and which cause no adverse effects on the body.

As used herein, "effective amount" means the amount of a bioactive agent that is sufficient to provide the desired local or systemic effect and performance at a reasonable risk/benefit ratio as would attend any medical treatment.

As used herein, "administering" and similar terms means delivering the composition to the individual being treated such that the composition is capable of being circulated systemically. Preferably, the compositions of the present invention are administered by the subcutaneous, intramuscular, transdermal, oral, transmucosal, intravenous, or intraperitoneal routes. Injectables for such use can be prepared in conventional forms, either as a liquid solution or suspension, or in a solid form that is suitable for preparation as a solution or suspension in a liquid prior to injection, or as an emulsion. Suitable excipients that can be used for administration include, for example, water, saline, dextrose, glycerol, ethanol, and the like; and if desired, minor amounts of auxiliary substances such as wetting or emulsifying agents, buffers, and the like can be used. For oral administration, it can be formulated into various forms such as solutions, tablets, capsules, etc.

Reference will now be made to the exemplary embodiments and specific language will be used herein to describe the same. It will nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention.

One aspect of the present invention provides a multi-block copolymer composition which when placed in an aqueous medium, forms a solution at low temperatures and gels at high temperatures. More particularly, the present invention provides a biodegradable multi-block copolymer having an improved release profile and control of the release rate of various drugs. Particularly, the present invention provides a multi-block copolymer comprising at least two ABA-type tri-block copolymers which are covalently connected through a biodegradable dicarboxylic linkage, wherein A is a polyethyleneoxide block, B is a polypropyleneoxide block, a polybutyleneoxide block or a combination thereof, and wherein said multi-block copolymer has an hydroxyl or ionic group at both terminal ends.

The multi-block copolymer of the present invention forms a hydrogel when it reaches a sufficient concentration and/or above a critical temperature and thereby shows sol-gel phase transition and is biodegradable. In the multi-block copolymer of the present invention, the PEO-PPO (or PBO)-PEO blocks are connected through biodegradable dicarboxylic linkages, and have a high molecular weight which provides for improved gel maintenance properties. Furthermore, the ionic terminal end provides for sustained drug release from the gel.

One embodiment of the present invention is a multi-block copolymer which can be represented by the following chemical formula 3:

M-X—O—[PEO—Y—PEO—C(=O)—R—C(=O)—O]$_n$—PEO—Y—PEO—O—X-M    Chemical formula 3

Wherein PEO is a polyethylene oxide block, Y is PPO or PBO or combinations of PPO and PBO, wherein PPO is a polypropylene oxide block and PBO is a polybutylene oxide block, X is H or an anion group, n is an integer ranging from 1 to 100, R is —(CH$_2$)$_m$— or an aryl having C$_{m'}$, 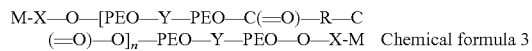

where m is an integer ranging from 0 to 20, m' is an integer ranging from 6 to 12, and M is H or a cation group, with the proviso that M and X can not both be H, and M cannot be present when X is H.

Preferably, X is an anion group selected from the group consisting of —$SO_3^-$, —$PO_3^{2-}$ and —$C(=O)$—R—$C(=O)$—$O^-$, and M is a cation group selected from the group consisting of Li, Na, K, Ag, Au, Ca, Mg, Zn, Fe, Cu, Co, and Ni.

More preferably, the multi-block copolymer of the present invention may be represented by the following chemical formula 4:

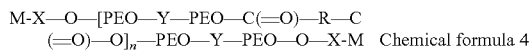
M-X—O—[PEO—Y—PEO—C(=O)—R—C(=O)—O]$_n$—PEO—Y—PEO—O—X-M   Chemical formula 4 wherein PEO is polyethylene oxide, Y is PPO or PBO or combinations of PPO and PBO, wherein PPO is a polypropylene oxide block and PBO is a polybutylene oxide block, X is —H, —$SO_3^-$, —$PO_3^{2-}$, or —$C(=O)$—R—$C(=O)$—$O^-$, n is an integer ranging from 1 to 100, R is —$(CH_2)_m$— or an aryl having $C_{m'}$, where m is an integer ranging from 0 to 20, m' is an integer ranging from 6 to 12, and M is —H, a monovalent or divalent cation group, with the proviso that M and X can not both be H, and M cannot be present when X is H.

The polyethyleneoxide block in the multi-block copolymer consists of ethylene oxide units having a unit number ranging from about 2 to 2000, preferably about 5 to 500, more preferably about 80 to 120. In the above formula 3, the unit number of each ethylene oxide of the two PEO blocks may be the same or different. The unit number of propyleneoxides or butyleneoxides in the polypropyleneoxide or polybutyleneoxide blocks is within the range from 2 to 2000, preferably from about 20 to 500, and more preferably is about 30 to 250.

The multi-block copolymer of the present invention has a weight average molecular weight ranging from 40,000 Daltons to 1,000,000 Daltons, preferably from 40,000 Daltons to 500,000 Daltons, and more preferably is from 80,000 Daltons to 130,000 Daltons.

The ratio of ethylene oxide units to propylene oxide or butylene oxide units in a PEO-PPO (or PBO)-PEO block can be adjusted in order to vary the properties of the polymer. For example, when it is required that the multi-block copolymer maintain its water-solubility, the unit ratio between the PEO and PPO or PBO in the multi-block copolymer ranges from about 0.2:1 to about 40:1, preferably from 1:1 to 7.5:1, and more preferably from 1:1 to 5:1. The PEO block is included in an amount of 10 to 85 wt %, preferably 40% to 85 wt % of the PEO-PPO (or PBO)-PEO units.

The term "multi-block" copolymer in the present invention refers to a copolymer wherein a polyethyleneoxide block is linked to a polypropyleneoxide or polybutyleneoxide block, which is, in turn, linked to a polyethyleneoxide block and the resulting PEO—PPO (or PBO)—PEO blocks are connected through biodegradable dicarboxylic linkages.

The term "dicarboxylic linkage" in the present invention refers to an ester linkage formed by the reaction of an alkyl or aryl compound having two carboxylic groups in one molecule such as oxalic acid, malonic acid, succinic acid, adipic acid and so on with a terminal OH group of a PEO—PPO or PBO—PEO block. The dicarboxylic linkage can be provided by an alkyl dicarboxylic acid selected from the group consisting of oxalic acid, malonic acid, malic acid, succinic acid, glutaric acid, adipic acid, pimelic acid, sebacoyl acid, suberic acid, and dodecanoic acid. The dicarboxylic linkage can also be provided by an unsaturated dicarboxylic acid such as fumaric acid or maleic acid, or by an aryl dicarboxylic acid such as phthalic acid, and terephthalic acid.

As previously stated, the dicarboxylic linkage can be ester-linked to the hydroxyl group which is present at both terminal ends of the PEO-PPO (or PBO)-PEO blocks. The ester linkage can be degraded into a carboxylic acid and PEO-PPO (or PBO)-PEO units by hydrolysis or enzymatically in a living body.

Both terminal ends of the multi-block copolymer of the present invention are hydroxyl or ionic groups. The ionic terminal end is preferably an anionic group such as —$SO_3^-$, —$PO_3^{2-}$, —$C(=O)$—R—$C(=O)$—$O^-$ and so on. A salt corresponding to the anionic group is formed with a monovalent metal cation such as Li, Na, K, Ag, or Au or a divalent metal cation such as Ca, Mg, Zn, Fe, Cu, Co or Ni.

Particularly, the one or more of multi-block copolymer of the present invention having anionic groups at both terminal ends can form a more stable gel with a divalent cationic metal because the above multi-block copolymer and the metal form a complex, and thus can be useful as a carrier for sustained drug release. When the multi-block copolymer of the present invention, having an anionic group, is mixed with a cationic drug in an aqueous solution, it forms an ion salt. The ion salt reduces the initial release rate of the drug from the multi-block copolymer gel and thus improves sustained release of drug. When a divalent cationic metal salt such as calcium chloride, zinc chloride, or magnesium chloride is added to a mixed solution of the multi-block copolymer of the present invention having anionic groups at its terminal ends and a drug having anionic group, the divalent metal cation forms a complex with the drug and the multi-block copolymer, which allows sustained release of drugs from the gel. Therefore, the multi-block copolymer of the present invention can be applied as a non-ionic and ionic drug delivery system for controlled drug release.

The multi-block copolymer composition of the present invention can be made using PEO-PPO (or PBO)-PEO blocks, which are available commercially and are called a poloxamer. A poloxamer is a block copolymer where a polyethylene oxide (PEO) hydrophilic block and a polypropylene oxide (PPO) hydrophobic block are linked in the form of a tri-block PEO-PPO-PEO by an ether bond, and which has a weight average molecular weight of 1,000 Daltons to 20,000 Daltons and has a terminal hydroxyl group. In the present invention, poloxamer 188 (Pluronic® F-68), and poloxamer 407 (Pluronic® F-127) can be used. The multi-block copolymer of the present invention is prepared using a purified or non-purified poloxamer. Purified poloxamer is more preferable for use in the preparation of large molecular weight multi-block copolymers of the present invention. Purification of the poloxamer is preformed by one of the following processes: it is dissolved in methylenechloride and precipitated in hexane, or it is separated in n-propanol/H2O solvent by layer-separation as disclosed in U.S. Pat. No. 5,800,711 which is incorporated herein by reference.

The present invention also provides a method for preparing a multi-block polymeric composition wherein a triblock copolymer of polypropyleneoxide or polybutyleneoxide blocks is positioned between two polyethyleneoxide blocks, said triblock copolymers are connected by biodegradable dicarboxylic linkages.

The present invention provides a method for a preparing a multi-block polymer including terminal hydroxyl ends comprising:

1) preparing a reaction solution containing a predetermined amount of PEO-Y-PEO, slowly adding 0.5 to 1.0 equivalents of dicarboxylic acid dihalide based on 1 equivalent of terminal end hydroxyl groups of the PEO-Y-PEO to the reaction solution and allowing the reaction to proceed for a predetermined number of hours;

2) adding an additional 0.1 equivalents of PEO-Y-PEO to the above reaction solution to react until the reaction is completed;

3) precipitating the produced multi-block copolymer in an ether or hexane solvent and then dissolving the precipitate in alcohol; and 4) slowly adding ether or hexane so that the volume ratio of alcohol/ether or hexane is 1/1 to 1/20 to precipitate the multi-block copolymer.

The present invention provides a method for a preparing a multi-block polymer, including the terminal carboxylic ends, which includes the following processes:

1) preparing a reaction solution containing a predetermined amount of PEO—Y—PEO, slowly adding 0.5 to 1.0 equivalents of dicarboxylic acid dihalide based on 1 equivalent of the terminal end hydroxyl groups of the PEO—Y—PEO to the reaction solution and allowing the reaction to proceed for a predetermined number of hours;

2) adding more than 1 equivalent of additional dicarboxylic acid dihalide based on an equivalent of hydroxyl groups of the PEO-Y-PEO terminal end to the reaction solution to react until the reaction is completed;

3) precipitating the produced multi-block copolymer in an ether or hexane solvent and then dissolving the precipitate in alcohol; and 4) slowly adding ether or hexane so that a volume ratio of alcohol/ether or hexane is 1/1 to 1/20 to precipitate the multi-block copolymer.

The present invention also provides a method for preparing a multi-block copolymer having metal carboxylate salts at both terminal ends of the multi-block copolymer comprising:

1) dissolving a polymer having carboxylic groups at both terminal ends in a solvent capable of being mixed with water, such as acetone, acetonitrile, or dioxane, and 2) neutralizing the multi-block solution with sodium carbonate, sodium bicarbonate, calcium chloride, zinc chloride, magnesium chloride, iron chloride, copper chloride, silver nitrate, potassium chloride, or lithium chloride followed by dialysis.

Alternatively, a multi-block copolymer having metal carboxylate salts except sodium carboxylate salt at both terminal ends of the multi-block copolymer can be prepared as the following method comprising:

treating a polymer having sodium carboxylate at both terminal ends with an aqueous solution containing calcium chloride, zinc chloride, magnesium chloride, iron chloride, copper chloride, silver nitrate, potassium chloride, or lithium chloride.

The present invention also provides a method for preparing a multi-block copolymer having a sulfuric acid, phosphoric acid, or metal salt thereof at its polymer terminal end, comprising:

1) dissolving a multi-block polymer having a terminal hydroxyl group in a solvent and reacting that with a sulfate trioxide pyridine complex ($C_5H_5NSO_3$) or phosphorous oxychloride ($POCl_3$); and 2) optionally neutralizing the reaction mixture with sodium carbonate, sodium bicarbonate calcium chloride, zinc chloride, magnesium chloride, iron chloride, copper chloride, silver nitrate, potassium chloride, or lithium chloride to prepare a multi-block copolymer having a metal salt at its polymer terminal end.

In the case where the terminal ends of the multi-block polymer is another anion group, it can be prepared using a conventional well-known method.

In the above reactions, the dicarboxylic acid dihalide can be directly reacted as a dicarboxylic linker. Also, when the dicarboxylic acid itself is a starting material, the dicarboxylic acid can be activated with oxalyl halide to convert it into a dicarboxylic acid dihalide which can then be used. The reaction can be performed with solvent or without solvent. Usable reaction solvents includes dichloromethane, chloroform, tetrahydrofuran, acetonitrile, acetone, toluene, dioxane and so on.

The polymerization reaction rate and polymerization degree, which determine the average molecular weight of the polymer, can be controlled by adjusting the reaction temperature and reaction time. The reaction temperature can be changed depending on the boiling point of the reaction solvents but it preferably ranges from 60 to 120° C. The reaction time preferably ranges from about 12 hours to 72 hours.

In order to increase the reaction rate, a catalyst such as tin octoate, zinc chloride and so on can be used, or an amine such as pyridine, dimethylaminopyridine, imidazole, triethylamine and so on can be used in an amount twice the number of equivalents based on one equivalent of the dicarboxylic acid. However, in order to obtain a high purity of the polymer, it is preferable that a catalyst or amine not be used.

The polymerized polymer can be purified by well-known methods, and preferably by precipating it in a solvent in which the reaction material is dissolved whereas a polymerized polymer is not dissolved.

A method for a preparing the multi-block copolymer of the present invention is exemplified as follows.

First, a dicarboxylic acid dichloride, which is diluted in a reaction solvent in the amount of 0.5 to 1.0 equivalents based on an equivalent of hydroxyl group of the poloxamer terminal end, is slowly added to a reaction vessel containing a poloxamer over more than 6 hours. The reaction is performed for more than 12 hours. The reaction temperature can be changed depending on the kind of solvent used. In the case of performing the reaction without a solvent, it is preferable that it is performed at a temperature ranging from 40 to 120° C. and within 24 hours.

After the reaction, 0.1 equivalents of poloxamer dissolved in a reaction solvent is again added to the reaction solution, and then is reacted for more than 2 hours and then precipitated in ether solvent in order to obtain a multi-block polymer having the terminal hydroxy ends of the present invention. The precipitate obtained is dissolved in methanol, and then diethyl ether is slowly added so that the mixed volume ratio of methanol/ether may range from 1/1 to 1/20, and preferably from 1/5 to 1/10, in order to percipitate polymer again and purify it. The precipitate is dissolved in an acetone aqueous solution, is then treated with an anion exchange resin retrieving a polymer having carboxyl terminal ends, which is then diaylized using a dialysis tube with a molecular weight cut-off of 40,000 Daltons. The diolysate is then freeze-dried obtaining a multi-block poloxamer having terminal hydroxyl ends.

A multi-block copolymer having a terminal carboxylic end is obtained as follows: an excess of more than 1 equivalent of dicarboxylic acid dichloride, based on the number of equivalents of the hydroxyl group of the poloxamer terminal end, is added after the polymerization reaction, which is then reacted for more than 2 hours and then ether is added to precipitate a polymer. The precipitate obtained is dissolved in methanol, and then ether is slowly added so that the mixed volume ratio of methanol/ether ranges from 1/1 to 1/20, preferably from 1/5 to 1/10, to precipitate the polymer again, and to purify it. A multi-block poloxamer having carboxylic terminal ends is so obtained. The copolymer is dissolved in an acetone aqueous solution and is neutralized with sodium carbonate or sodium bicarbonate to obtain a copolymer wherein sodium carboxylate salts are present at both terminal ends of the multi-block poloxamer.

The multi-block copolymer having sodium carboxylate salts present at both terminal ends is mixed with an excess of an aqueous solution of calcium chloride, magnesium chloride, zinc chloride, iron chloride, copper chloride, silver nitrate, potassium chloride, or lithium chloride and so on, and is then dialyzed to prepare a multi-block copoloxamer having a monovalent or divalent metal salt at its terminal end.

In order to obtain a multi-block copolymer having sulfate group or phosphate group at its terminal end, a multi-block copoloxamer having both hydroxyl terminal ends is dissolved in dimethylformamide, is then reacted with a sulfate trioxide pyridine complex ($C_5H_5NSO_3$) or phosphorous oxychloride ($POCl_3$) at 60° C. for 10 hours, the product obtained is then dilluted with distilled water and dialyzed. Subsequently, a matal salt aqueous solution such as sodium bicarbonate is added to neutralize the above solution, followed by freeze-drying.

Both terminal ends of the synthesized multi-block copolymer of the present invention can be identified using nuclear magnetic resonance (NMR). The synthesized multi-block copolymer is reacted with trimethylsilylchloride (TMS—Cl) in the presence of triethylamine and then its spectrum is measured using nuclear magnetic resonance. When its terminal group is a hydroxyl group, a signal peak corresponding to the trimethylsilyl proton is shown at 0.12 ppm and when it is a carboxyl terminal group, the signal peak is shown at 0.3 ppm. Using these results, the terminal group of the synthesized multi-block copolymer can be determined.

The multi-block copolymer of the present invention forms a hydrogel when placed in an aqueous medium at sufficient concentration and above a critical temperature. The term of "sol-gel phase transition" in the present invention means that it is present as a flowable liquid below a critical temperature and is changed into a gel above a critical temperature, and if the temperature is lowed below a critical point, it is reversibly changed into a flowable liquid. The gelation temperature depends on the type and molecular weight of the polymer, the concentration of the copolymer aqueous solution, the absence or presence of a salt, the proton concentration and so on. The critical temperature ranges from 5 to 37° C. The multi-block copolymer of the present invention can be dissolved in water at a concentration of 2 to 40 wt % and its gelation temperature ranges from 10 to 50° C.

The multi-block copolymer of the present invention can form a gel at a relatively low concentration of 10% as compared to a poloxamer and thus has decreased toxicity in the living body. It also has a higher gelation temperature than a poloxamer and thus is easily injected. The multi-block copolymer of the present invention is also increased in molecular weight by multi-blocking with PEO-PPO (or PBO)-PEO units and thus a multi-block copolymer with a high molecular weight can be maintained as a gel in a living body or aqueous solution for a long time. Therefore, in the case where the multi-block copolymer of the present invention is used as a drug carrier, it can continuously release drug for more than 24 hours even with one time once injection. Therefore, the present invention can overcome the problem of using a conventional poloxamer 407 as a delivery system because the poloxamer has a short drug sustained duration of drug release.

The multi-block copolymer of the present invention has hydrolytic properties due to ester binding of its dicarboxylic linkage and is degraded into low molecular weight PEO—PPO (or PBO)—PEO blocks and dicarboxylic acids which are water-soluble and easily excreted from the living body. Therefore adverse effects caused by the presence of a large polymer in the body can be avoided. The degradation rate of the multi-block copolymer depends on the number of dicarboxylic linkages and thus the size and number of each block can be adjusted to control the hydrolysis rate and size of the hydrolyzed product.

The present invention also provides a pharmaceutical composition comprising the present biodegradable multi-block copolymer. The multi-block polymer of the present invention can be a carrier for the delivery of drugs. The hydrogel of the multi-block copolymer of the present invention can deliver drugs and can be implanted or injected into a body and deliver drugs. The hydrogel formed by the multi-block copolymer of the present invention is preferably used for the sustained release of a drug in the body.

After a drug is added to a solution or suspension including the multi-block copolymer of the present invention, it can be injected as an aqueous solution into a living body at a low temperature, the drug containing multi-block copolymeric solution forms a drug-containing depot in a gel state at body temperature and slowly releases drug from the gel when the dicarboxylic linkages of multi-block copolymer are degraded by hydrolysis. The multi-block copolymer of the present invention may also be mixed with a drug in an aqueous solution or an organic solvent and then can be used as a drug carrier in the form of a micro-sphere, nano-particle, stripe, film and so on to be injected into a living body.

The drugs which can be used in the drug delivery system using the multi-block copolymers of the present invention can be any drug, for example non-ionic and ionic drugs. The drug may include but is limited to small molecules, peptides, proteins, polysaccharides, nucleotides and so on. The drug may preferably be an ionic drug and particularly a peptide or protein having a large number of carboxylic groups and amino ionic groups in its molecule. Exemplary peptides or proteins includes growth hormone (GH), interferon (IFN), granulocyte colony stimulation factor (G-CSF), granulocyte macrophage colony stimulating factor (GMCSF), erythropoietin (EPO), interleukin (IL), fibroblast growth factor, follicle stimulating hormone (FSH), macrophage colony stimulating factor (M-CSF), nerve growth factor (NGF), octreotide, insulin, insulin-like growth factor (IGF), calcitonin, tumor necrosis factor (TNF), vascular endothelial growth factor (VEGF), epidermal growth factor (EGF), platelet-derived growth factor (PDGF), bone morphogenetic protein (BMP), tissue plasminogen activator (TPA), thrombopoietin (TPO), tissue growth factor, tumor necrosis factor (TNF) and so on. The peptide and protein may be natural, synthetic, native, glycosylated, modified with a polymer such as PEG, and biologically active fragments and analogs thereof.

Therefore, another embodiment of the present invention is a pharmaceutical composition comprising the multi-block copolymer of the present invention and an effective amount of a bioactive agent. The bioactive agent can be included within the range form 0.01% to 50%. The multi-block copolymer aqueous solution can be used as a drug carrier if it shows a phase transition and can be preferably used in a concentration of 0.5 to 50%.

To be used as a drug carrier for peptides or proteins, it is necessary to make the multi-block copolymer of the present invention in the state of an aqueous solution. The multi-block copolymer of the present invention is not dissolved at room temperatures, such as about 25° C., but has a high solubility at low temperature, such as about 4° C. Therefore, the multi-block copolymer is preferably dissolved at low temperature. The amount of multi-block polymer that can be dissolved is limited depending on its molecular weight. A multi-block copolymer having molecular weight of 100,000 can be dissolved in water at a maximum of 30%, preferably 4 to 20%. Therefore, when peptide, protein or water-soluble drugs are mixed with the multi-block copolymer aqueous solution at a low temperature and is administrated subcutaneously or orally, the aqueous solution is changed into a hydrogel at body temperature which the releases the peptide, protein or water-soluble drug slowly.

The multi-block copolymer of the present invention can be made in the form of micro-spheres or nano-particles by generally well-known methods. For example, the polymer can be dissolved in methylene chloride and precipitated at 37° C. water, normal saline, PBS solution or an aqueous solution where 0.1% to 2% of the polymer of the present invention. Alternatively, a stripe or rod of the multi-block copolymer of the present invention can be prepared with freeze-dried polymer by extrusion, compressing, or adherence molding. Also, films of the multi-block copolymer of the present invention can be made by heating at predetermined temperature (60° C. to 120° C.).

PEG, hyaluronic acid, dextran, gelatin, collagen, chitosan, poloxamer 407, poloxamer 188, methylcellulose (MC), ethylcellulose (EC), hydroxyethylcellulose (HEC), methylhydroxyethylcellulose (MHEC), hydroxymethylcellulose, hydroxypropylmethylcellulose (HPMC), hydroxypropylcellulose and so on may be added to the multi-block copolymer of the present invention in an amount of 0.1 to 50%, which is used as sustained release drug delivery by being prepared in the form of a mixed sol-gel depot-type drug carrier, microsphere, nanosphere, stripe, rod, or film. When it is prepared in the form of the mixed drug carrier, the gelation temperature or gel strength of a polymer of the present invention can be changed.

A delivery method and administration amount of the above described drug can be varied depending on the physiological activity of the drug, its site of action in a living body, physicochemical properties and so on. The physicochemical properties of the polymer of the present invention and hydrophilicity/hydrophobicity of the drug can be controlled.

The following examples will enable those skilled in the art to more clearly understand how to practice the present invention. It is to be understood that, while the invention has been described in conjunction with the preferred specific embodiments thereof, that which follows is intended to illustrate and not limit the scope of the invention. Other aspects of the invention will be apparent to those skilled in the art to which the invention pertains.

EXAMPLE 1

Synthesis of Multi-block Polymer Using Succinyl Dichloride Linkage 10 g of Pluronic® F127 (BASF; poloxamer 407) was added with a magnetic rod into a 100 ml flask, heated the flask to 120° C. in an oil double boiler while reducing the pressure to under 1 torr for 2 hours to remove any moisture contained in the polymer. The pressure-reduction was released and the reaction temperature was set at 100° C. while under flowing nitrogen and 100 ml of acetonitrile was added to the flask. The reaction flask was mounted with a dean stark and cooler to allow 20 ml of distilled acetonitrile to pass through the dean stark and thus remove any moisture contained in the reaction material. Then, 96 ul (corresponding to 1 equivalent based on the polymer) of succinyl dichloride was added to the reservoir of the dean stark and reacted for 24 hours. In order to substitute the terminal groups of the synthesized multi-block poloxamer-407 with a carboxyl group after the 24 hours of reaction, 96 ul of succinyl chloride was added again to the reservoir of the dean stark and was reacted for additional 24 hours. The synthesized multi-block poloxamer was precipitated in 1 L of diethylether and then filtered to yield a product (8.2 g).

The product thus obtained was dissolved in 16 ml of methanol, and was purified twice through precipitation in diethylether and filtration. Then it was vacuum-dried to obtain a multi-block poloxamer (5.7 g) with a narrow molecular weight distribution.

The weight average molecular weight of the multi-block poloxamer was determined to be 90,700 Daltons through GPC and its synthesis was confirmed using $^1$H-NMR (FIG. 1).

EXPERIMENTAL EXAMPLE 1

Analysis of the Terminal Ends of the Multi-block Polymer

In order to confirm that the terminal group of the multi-block poloxamer synthesized according to the Example 1 was converted into a carboxyl group, $^1$H-NMR was measured after reacting the terminal group of the synthesized multi-block poloxamer with trimethylsilylchloride (TMS-Cl).

(1) Synthesis of Poloxamer-407 Disuccinate 10 g of Pluronic® F127 (BASF; poloxamer 407) was added with a magnetic rod into a 100 ml 1-mouth round-bottom flask, and heated while reducing the pressure to under 1 torr in an oil double boiler heated to 120° C. for 2 hours to remove moisture included in the polymer. The pressure-reduction was released and the reaction temperature was set at 50° C. while under flowing nitrogen and then 100 ml of acetonitrile was added to the flask. 5 ml of succinyl dichloride was added into the reaction vessel and reacted for 24 hours. The product was purified twice by being precipitated in an excessive of hexane and filtered. It was then vacuum-dried.

Figure 2:
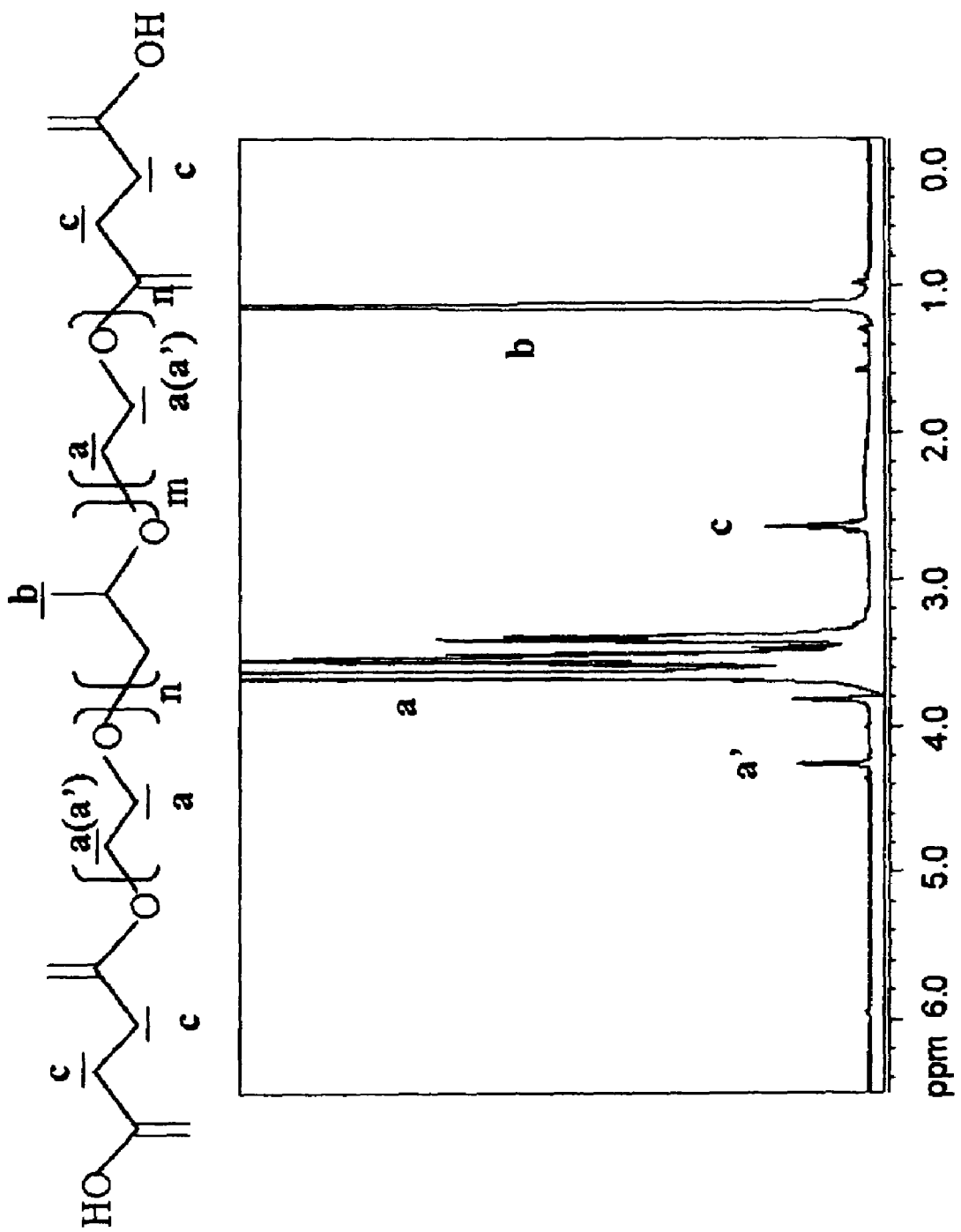
FIG. 2 is a $^1$H-NMR spectrum of poloxamer disuccinate (Experimental Example 1).

Poloxamer disuccinate was confirmed by measuring $^1$H-NMR (FIG. 2)

(2) Analysis of the Terminal Group of the Multi-block Polymer 20 mg of poloxamer-407 and 20 mg of poloxamer-407 disuccinate synthesized in the above example (1) were reacted with TMS-Cl (10 ul), and $^1$H-NMR analysis was performed. At analysis, 10 ul of pyridine was added as a catalyst.

Figure 3:
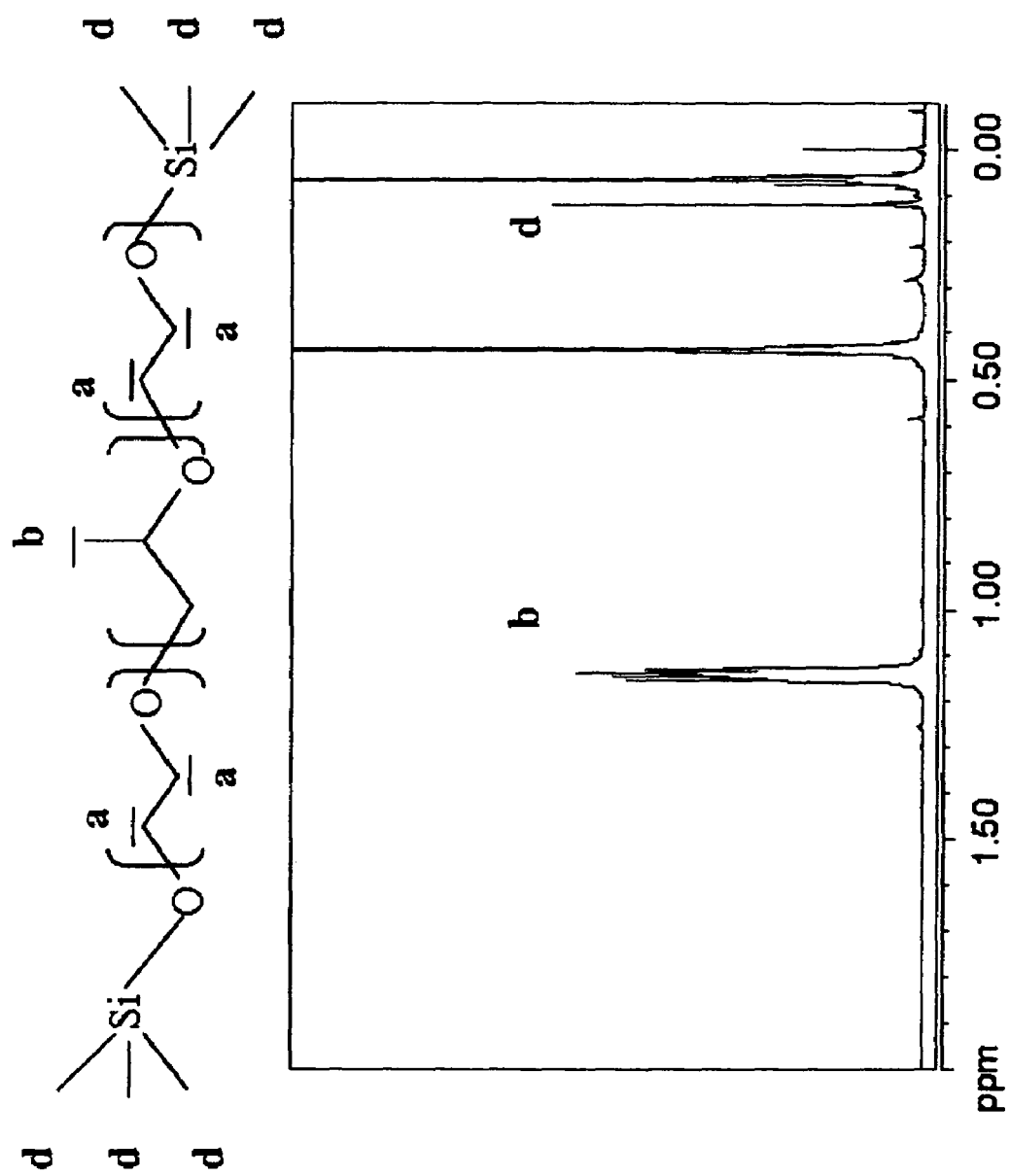
FIG. 3 is a $^1$H-NMR spectrum of poloxamer+(TMS-Cl/pyridine) (Experimental Example 1).
Figure 4:
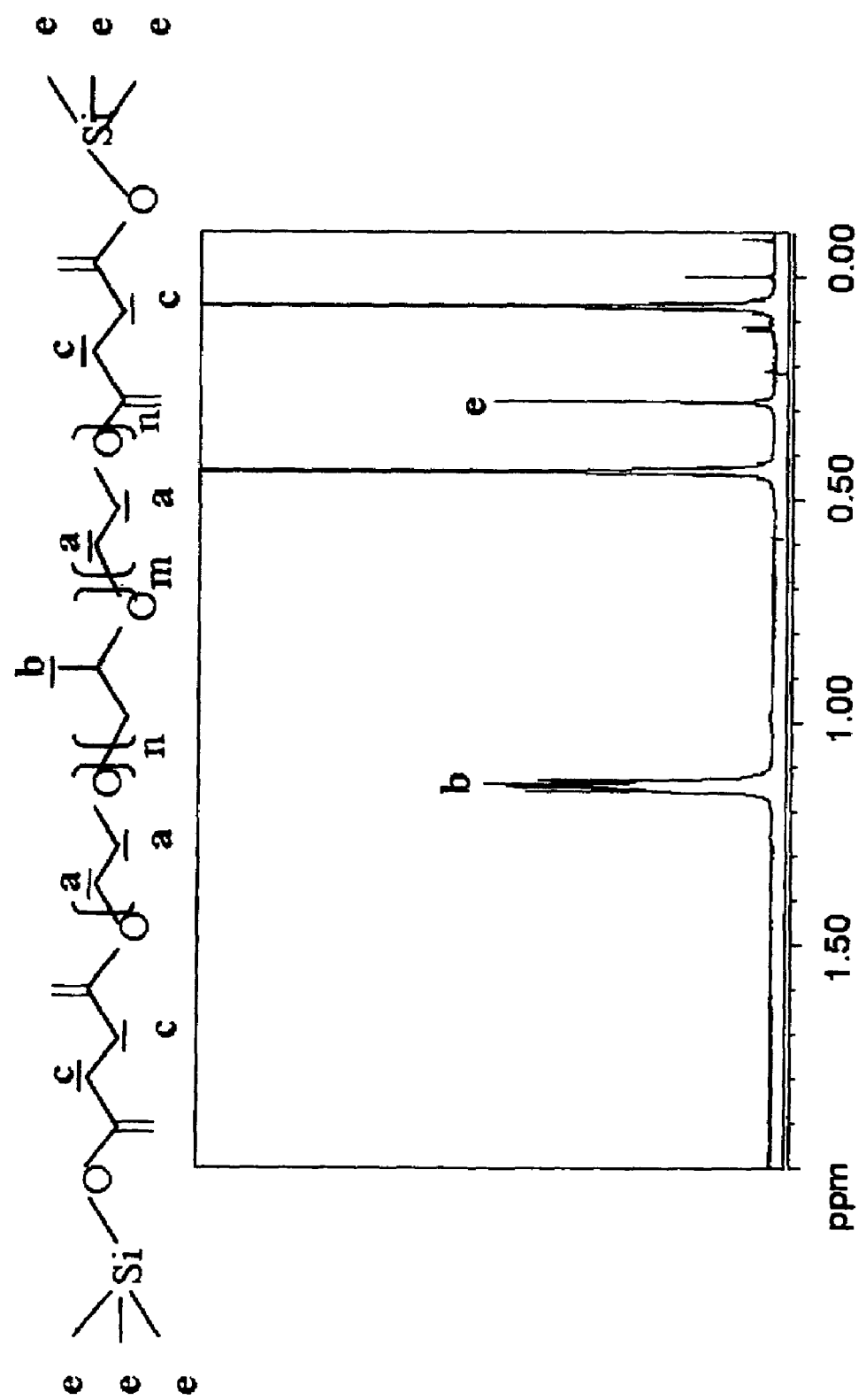
FIG. 4 is a $^1$H-NMR spectrum of poloxamer disuccinate+(TMS-Cl/pyridine) (Experimental Example 1).

Since all of the terminal groups of the poloxamer-407 were hydroxyl groups, the presence of the peak (0.12 ppm) of trimethyl of TMS-Cl confirmed the completion of the reaction of all the —OH groups (FIG. 3). Since all of the terminal groups of the poloxamer-407 disuccinate were carboxyl groups, the presence of the peak (0.29 ppm) of trimethyl of TMS-Cl confirmed completion of the reaction of all the —COOH groups (FIG. 4).

Figure 5:
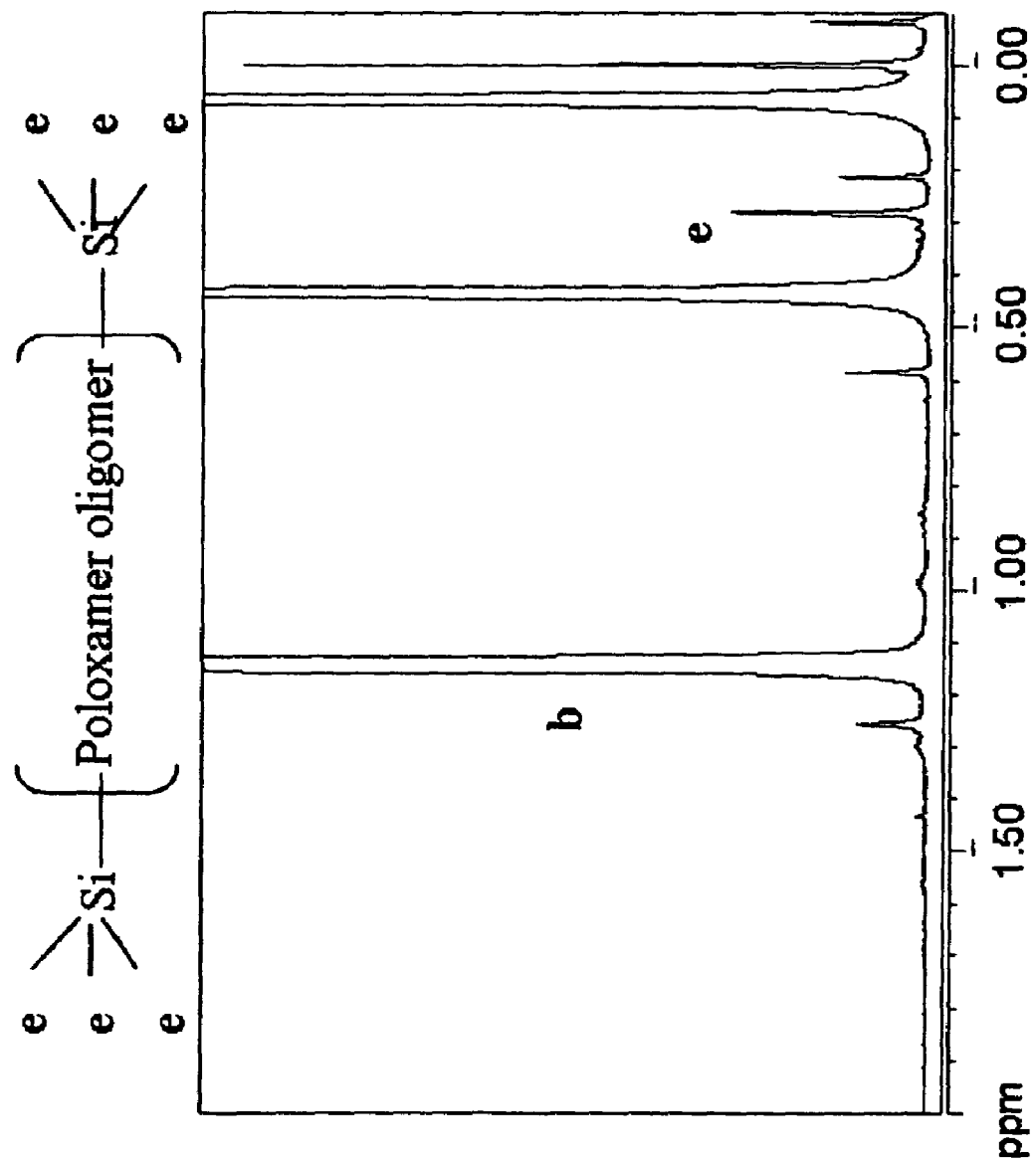
FIG. 5 is a $^1$H-NMR spectrum of a multi-block poloxamer+(TMS-Cl/pyridine) (Experimental Example 1).

Based on the data, the multi-block poloxamer synthesized according to Example 1 was analyzed by the same method using $^1$H-NMR (FIG. 5). Referring to the $^1$H-NMR spectrum, just the peak from the reaction of TMCS and —COOH was shown, but the peak from reaction of the TMCS and —OH is not shown. From the results as above, all of the terminal groups of the multi-block poloxamer-407 synthesized according to Example 1 were substituted with carboxyl groups.

EXAMPLE 2

Synthesis of a Multi-block Polymer Using an Oxalyl Dichloride Linkage

A multi-block poloxamer connected through an oxalyl group was synthesized by the same method as in Example 1, except that oxalyl dichloride was used as a dicarboxylic acid linker.

The multi-block copolymer obtained has a molecular weight of 91,300 Daltons.

EXAMPLE 3

Synthesis of a Multi-block Polymer Using an Adipoyl Dichloride Linkage

A multi-block poloxamer connected through an adipoyl group was synthesized by the same method as in Example 1, except that adipoyl dichloride was used as a dicarboxylic acid linker.

The multi-block copolymer obtained has a molecular weight of 96,300 Daltons.

EXAMPLE 4

Synthesis of a Multi-block Polymer Using a Suberoyl Dichloride Linkage

A multi-block poloxamer connected through a suberoyl group was synthesized by the same method as in Example 1, except that suberoyl dichloride was used as a dicarboxylic acid linker. The obtained multi-block copolymer has a molecular weight of 97,800 Daltons.

EXAMPLE 5

Synthesis of a Multi-block Polymer Using a Sebacoyl Dichloride Linkage

A multi-block poloxamer connected through a sebacoyl group was synthesized by the same method as in Example 1, except that sebacoyl dichloride was used as a dicarboxylic acid linker. The multi-block copolymer obtained has a molecular weight of 124,000 Daltons.

EXAMPLE 6

Synthesis of a Multi-block Polymer Using a Dodecanoyl Dichloride Linkage

A multi-block poloxamer connected through a dodecanoyl group was synthesized by the same method as in Example 1, except that dodecanoyl dichloride was used as a dicarboxylic acid linker. The multi-block copolymer obtained has a molecular weight of 104,000 Daltons.

EXAMPLE 7

Synthesis of a Multi-block Polymer Using a Terephthaloyl Dichloride Linkage

A multi-block poloxamer connected through a terephthaloyl group was synthesized by the same method as in Example 1, except that terephthaloyl dichloride was used as a dicarboxylic acid linker. The multi-block copolymer obtained has a molecular weight of 87,000 Daltons.

EXAMPLE 8

Synthesis of a Multi-block Polymer Using a Fumaric Acid Linkage 10 g of fumaric acid and 22 g of oxalyl chloride (twice the equivalents of fumaric acid) was reacted in 50 ml of acetonitrile at 50° C. for 6 hours. After the reaction, excess oxalyl chloride was removed by reaction with fumaroyl dichloride under vacuum. A multi-block poloxamer connected through fumaric acid groups was synthesized using the above synthesized fumaroyl chloride as a linker by the same method as in Example 1. The multi-block copolymer obtained has a molecular weight of 85,400 Daltons.

EXAMPLE 9

Synthesis of a Multi-block Polymer Using a Maleic Acid Linkage

A polymer was prepared by performing the same method as in Example 8, except that maleic acid was used. The multi-block copolymer obtained has a molecular weight of 82,700 Daltons.

EXAMPLE 10

Synthesis of a Multi-block Polymer Using a Malic Acid Linkage

A polymer was prepared by performing the same method as in Example 8, except that malic acid was used. The multi-block copolymer obtained has a molecular weight of 84,000 Daltons.

EXAMPLE 11

Synthesis of Multi-block Polymer Having a Sodium Carboxylate Group at its Terminal End 10 g of the multi-block poloxamer having carboxyl groups at both the terminal ends, which was synthesized in Example 1, was dissolved in 50 ml of an acetonitrile solution. To the obtained solution, an aqueous solution of sodium hydrogen carbonate in a concentration of 1 g/ml was slowly added to neutralize the obtained solution until its pH reached pH 8. The solvent was removed from the obtained solution using a rotary evaporator. Then, the remaining polymer was dissolved in 50 ml of methylenechloride solution.

The unreacted sodium hydrogen carbonate was precipitated, and the precipitate was removed by filtration. The filtrated methylenechloride solution containing polymer was precipitated with 500 ml of diethyl ether and filtrated to obtain the multi-block polymer having sodium carboxylate salts at its terminal end.

EXAMPLE 12

Synthesis of Multi-block Polymer Having a $SO_3Na$ Group at its Terminal End 10 g of the multi-block polymer having terminal hydroxyl ends which was obtained as an intermediate in Example 1 was put into a 1-mouth flask, and dried in vacuum at 120° C. for 2 hours to remove moisture. The reaction temperature was lowered to 60° C., and the obtained product was then dissolved in 50 ml of an acetonitrile solution. 0.16 g of a sulfate trioxide pyridine complex was dissolved in the obtained solution. The resultant solution was reacted by stirring with a magnetic stirrer for 10 hours. The solvent was removed from the obtained polymer solution using a rotary evaporator, and the polymer was then dissolved in 50 ml of methylenechloride solution.

The unreacted sulfate trioxide pyridine complex was precipitated, and the precipitate was removed by filtration. The filtrated methylenechloride solution was precipitated with 500 ml of diethyl ether and filtrated to obtain the multi-block polymer having a $SO_3Na$ group at its terminal end.

EXAMPLE 13

Measurement of the Phase Transition Temperature of a Multi-block Polymer

Figure 6:
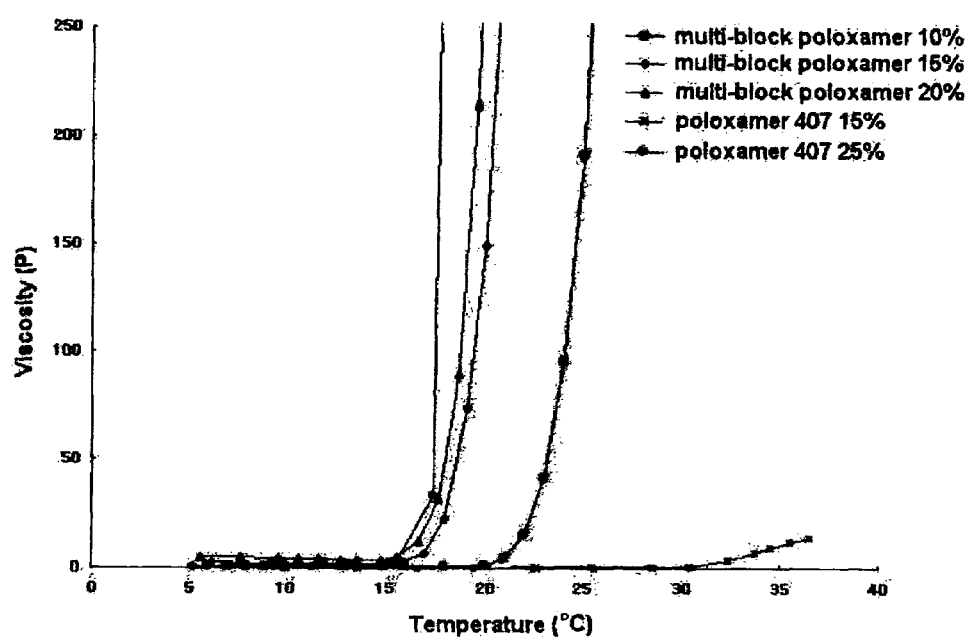
FIG. 6 is a graph showing a sol-gel phase transition profile of a multi-block poloxamer (Example 13).

In order to prepare 3 ml of 10 w/w %, 15 w/w % and 20 w/w % multi-block copolymer aqueous solutions, 176 mg, 353 mg and 529 mg of polymers according to Example 1 were added to 3 ml of distilled water and stirred at 4° C. for 2 hours in order to dissolved the copolymer thoroughly. The viscosity of the multi-block polymeric aqueous solution was measured using a Brookfield viscometer (model: RVDV II+) and thereby a phase transition temperature was determined (FIG. 6). The 15% aqueous poloxamer 407 solution was not gelated at above 37° C., body temperature, and the 25% aqueous poloxamer 407 solution was gelated at 17° C. On the contrary, the 10% aqueous multi-block polymer (having a molecular weight of about 100,000 Daltons) solution was gelated at 25.9° C., and the 15% aqueous solution was gelated at 20.5° C.

Accordingly the polymer of the present invention can be gelated at a relatively lower concentration compared to the poloxamer 407 solution. This relatively higher gelation temperature of the multi-block polymer makes it easy to inject it into a body using a syringe as compared to the poloxamer 407 solution.

EXAMPLE 14

In Vivo Release of Interferon-α from the Gel of a 15 w/w % Multi-block Copolymer Solution 0.106 ml of 1 mg/ml zinc acetate solution was added to 1.2 ml of 15 MIU/ml interferon-α solution and the pH of the solution was maintained from 5.0 to 8.0 to form a interferon-α-zinc complex. 212 mg (15 w/w %) of the multi-block copolymer (molecular weight 90,700 Daltons) according to Example 1 was added to the interferon-zinc complex solution and placed at 4° C. for more than 3 hours preparing an interferon multi-block copolymer solution.

When the solution was left at room temperature, it solidified at 21° C. changing into an uninjectable form.

The above prepared interferon-multi-block polymer solution was put into syringes at 4° C., each with 0.4 ml (30 MIU/rat) and was administrated subcutaneously to rats (SD rat 7 weeks, 200 g~220 g). In order to lower the skin temperature of the rats to 25° C., an ice bag was placed on the administration site was contacted with, ice bag for about 5~8 seconds.

Figure 7:
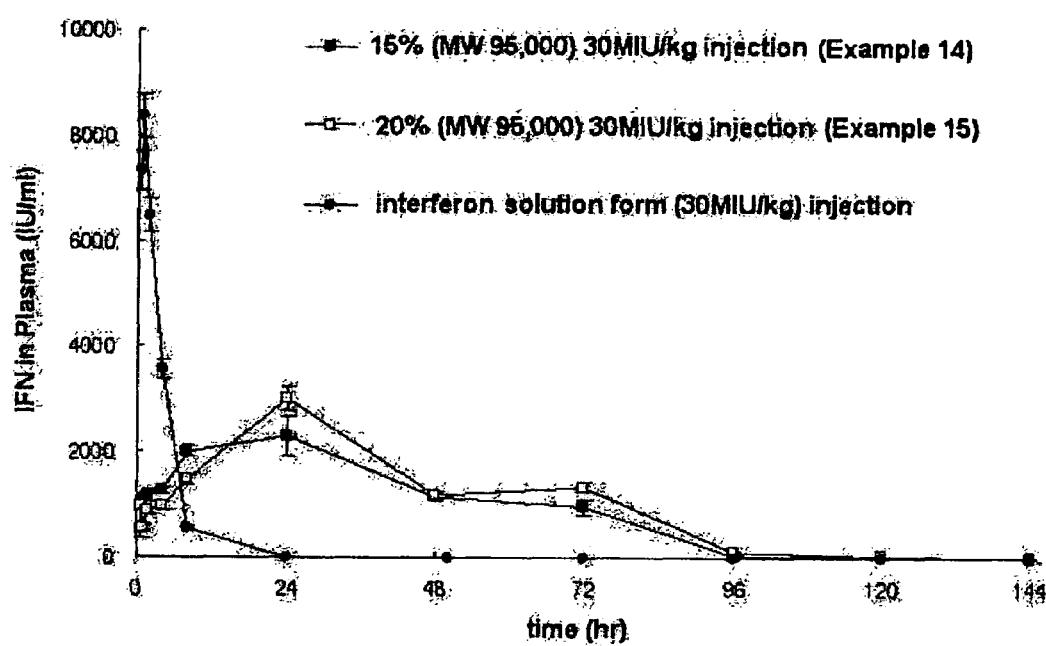
FIG. 7 is a graph showing the release profile of interferon-α from the hydrogel of the present invention (Examples 14 and 15).

After administration, 400 μl of whole blood was collected from the tail vein after 30 minutes, 1 hour, 2 hours, 4 hours, 8 hours, 1 day, 2 days, 3 days, 4 days, 5 days, and 6 days and the blood plasma were separated. Then, the interferon-α concentration in the blood was analyzed using an ELISA kit. As a result, the gel of the 15 w/w % multi-block copolymer slowly released interferon-α for more than 5 days after administration (FIG. 7).

EXAMPLE 15

In Vivo Release of Interferon-α from a Gel of a 20 w/w % Multi-block Copolymer Solution 0.106 ml of 1 mg/ml zinc acetate solution was added to 1.2 ml of 15 MIU/ml interferon solution and the pH was maintained from 5.0 to 8.0 to forming an interferon-zinc complex. 300 mg of a multi-block copolymer (molecular weight 90,700 Daltons) according to Example 1 was added to the interferon-zinc complex solution and placed at 4° C. for more than 4 hours to prepare an interferon multi-block polymer solution. The solution solidified at 18° C. changing into an uninjectable form. The solution was administrated to rats by the same method as in Example 13. As a result, it was confirmed that interferon was also released for more than 5 days (FIG. 7).

EXAMPLE 16

Figure 8:
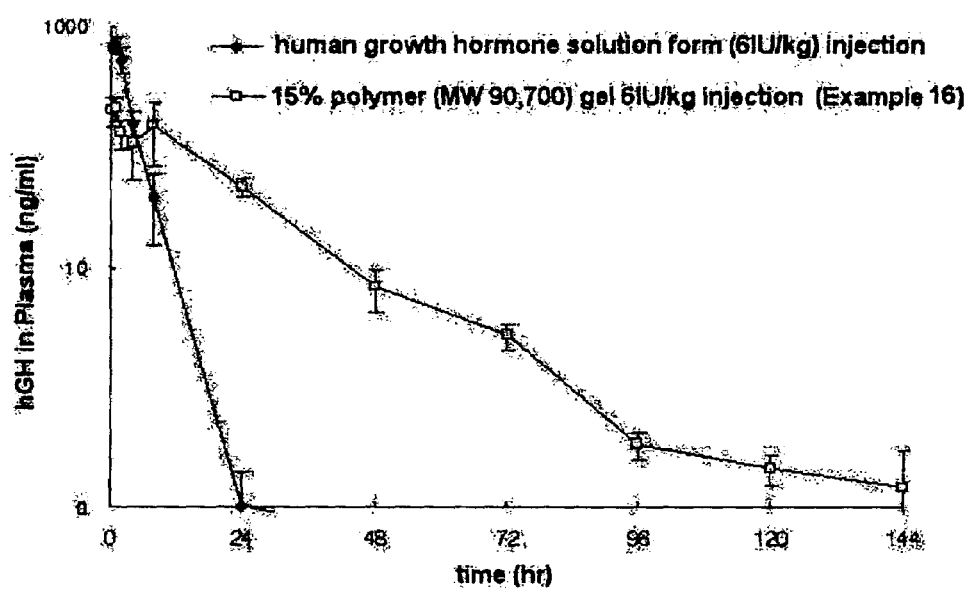
FIG. 8 is a graph showing the release profile of human growth hormone from the hydrogel of the present invention (Example 16).

In Vivo Release of Human Growth Hormone from a Gel of a 15 w/w % Multi-block Copolymer Solution 2.07 mg of human growth hormone freeze-dried powder was dissolved in 1.66 ml of water for injection to prepare 1.25 mg/ml of a human growth hormone solution. 293 mg of the multi-block copolymer (molecular weight 90,700 Daltons) according to Example 1 placed at 4° C. for 3 hours to prepare a 15 w/w % copolymer solution including human growth hormone. The solution was drawn into syringes at 4° C. with 0.4 ml (6 IU/kg) in each and was administrated subcutaneously to rats (7 weeks, 200 g~220 g) by the same method as in Example 13. As a result, it was confirmed that human growth hormone was released for more than 6 days (FIG. 8).

EXAMPLE 17

Figure 9:
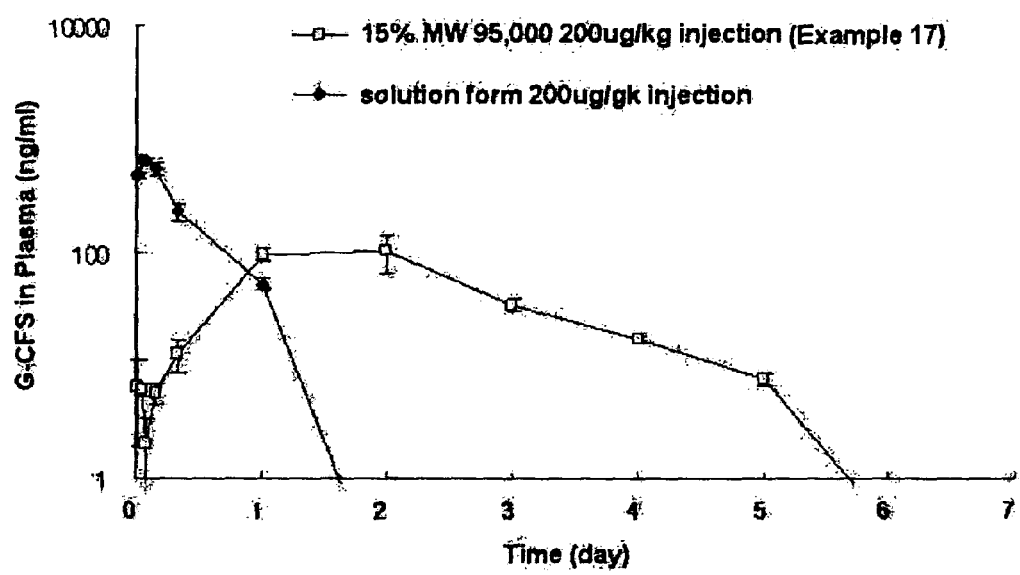
FIG. 9 is a graph showing the release profile of G-CSF from the hydrogel of the present invention (Example 17).

In Vivo Release of G-CSF from the Gel of a 15 w/w % Multi-block Copolymer Solution 100 μg/Ml concentration of G-CSF solution was diluted with normal saline or water for injection. 176 mg of the multi-block copolymer (molecular weight 90,700 Daltons) of Example 1 was placed at 4° C. for 3 hours to prepare a 15 w/w % copolymer solution including G-CSF. The solution was drawn into syringes at 4° C., each with 0.4 ml and was administrated to rats by the same method as in Example 13. As a result, it was confirmed that G-CSF was released for about 6 days (FIG. 9).

EXAMPLE 18

Figure 10:
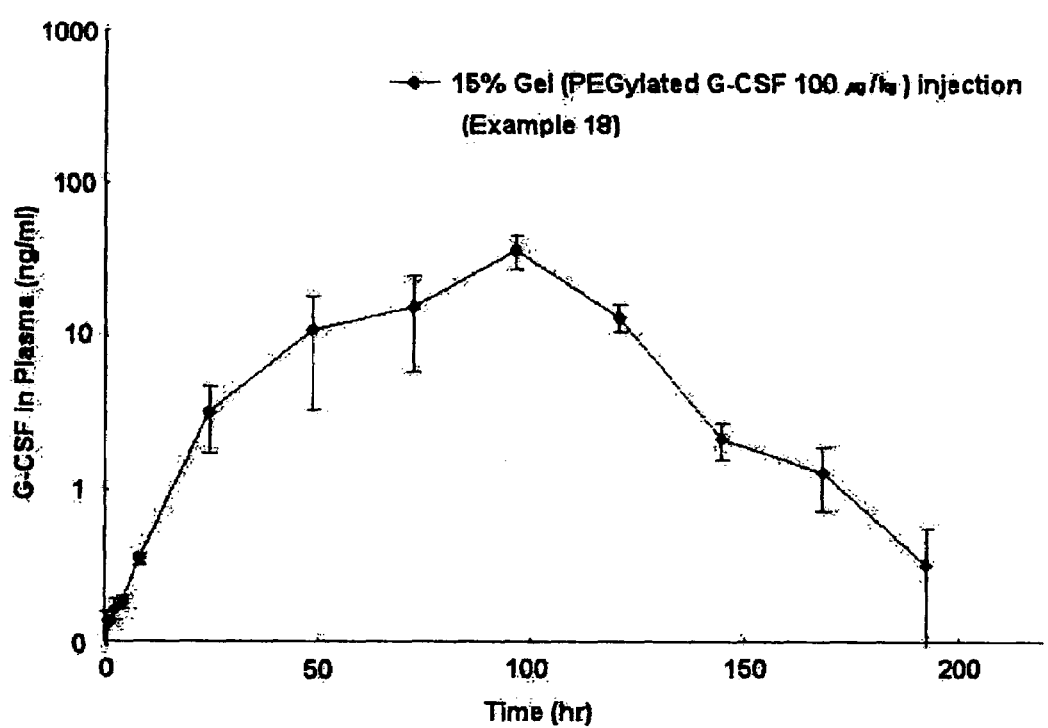
FIG. 10 is a graph showing the release profile of pegylated G-CSF from the hydrogel of the present invention (Example 18).

In Vivo Release of Pegylated G-CSF from the Gel of a 15 w/w % Multi-block Copolymer Solution 9 mg/ml of PEG-G-CSF was diluted to 125 μg/Ml. This solution and 317 mg of the multi-block copolymer (molecular weight 90,700 Daltons) of Example 1 were mixed at 4° C. for 3 hours to prepare a pegylated G-CSF polymer solution which shows gel transition depending on the temperature. The solution was drawn put into syringes at 4° C., each with 0.4 ml and administrated to rats by the same method as in Example 13. As a result, it was confirmed that G-CSF was released for about 8 days (FIG. 10).

It is to be understood that the above-described embodiments are only illustrative of the applications of the principles of the present invention. Numerous modifications and alternative embodiments can be derived without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth in the claims.

We claim:

1. A multi-block copolymer comprising at least two ABA-type tri-block copolymers which are covalently connected through a biodegradable dicarboxylic linkage, wherein A is a polyethyleneoxide block, B is a polypropyleneoxide block, a polybutyleneoxide block or a combination thereof, and wherein said multi-block copolymer has an ionic group at both terminal ends,
wherein the ionic group is a member selected from the group consisting of monovalent or divalent metal salt of $-SO_3^-$, $-PO_3^{2-}$, and $-C(=O)-R-C(=O)-O^-$, wherein, R is $-(CH_2)_m-$ or an aryl having $C_m'$, m is an integer ranging from 0 to 20, and m' is an integer ranging from 6 to 12.

2. The multi-block copolymer composition according to claim 1, the unit number of ethyleneoxide, and propyleneoxide or butyleneoxide is within the range from 2 to 2000, respectively.

3. The multi-block copolymer composition according to claim 1, wherein the unit ratio between A and B block ranges form 0.2:1 to 40:1.

4. The multi-block copolymer according to claim 1, has a weight average molecular weight ranging from 40,000 to 1,000,000 Daltons.

5. The multi-block copolymer composition according claim 1, wherein the biodegradable dicarboxylic linkage is derived from a member selected from the group consisting of oxalic acid, malonic acid, malic acid, succinic acid, glutaric acid, adipic acid, pimelic acid, sebacoyl acid, subenic acid, dodecanoic acid fumaric acid, maleic acid, phthalic acid and terephthalic acid.

6. A multi-block copolymer represented by the following formula:

wherein PEO is a polyethylene oxide block,
Y is PPO or PBO or combinations of PPO and PBO, wherein PPO is a polypropylene oxide block and PBO is a polybutylene oxide block,
X is an anion group selected from the group consisting of $-SO_3^-$, $-PO_3^{2-}$ and $-C(=O)-R-C(=O)-O^-$, wherein, R is $-(CH_m-$ or an aryl having $C_m'$, m is an integer ranging from 0 to 20, and m' is an integer ranging from 6 to 12,
n is an integer ranging from 1 to 100.

7. The multi-block copolymer according to claim 6, wherein M is a cation selected from the group consisting of Li, Na, K, Ag, Au. Ca, Mg, Zn, Fe, Cu, Co and Ni.

8. The multi-block copolymer according to claim 6, has a weight average molecular weight ranging from 40,000 to 1,000,000 Daltons.

9. The multi-block copolymer according to claim 6, wherein the unit ratio between the PEO and Y ranges from 0.2:1 to 40:1.

10. The multi-block copolymer according to claim 6, wherein Y has a weight average molecular weight ranging from 1,000 to 20,000 Daltons.

11. The multi-block copolymer according to claim 6, wherein the PEO—Y—PEO block is a poloxamer.

12. The multi-block copolymer according to claim 6, wherein R is a biodegradable dicarboxylic linkage is derived from a member selected from the group consisting of oxalic acid, malonic acid, malic acid, succinic acid, glutaric acid, adipic acid, pimelic acid, sebacoyl acid, suberic acid, dodecanoic acid, fumaric acid, maleic acid, phthalic acid and terephthalic acid.

13. A composition comprising a multi-block copolymer according to either one claim 1 or 6.

14. The composition according to claim 13, wherein the multi-block copolymer composition is in a form selected from the group consisting of gels, micro-spheres, nano-particles, stripes, rods and films.

15. A pharmaceutical composition comprising the composition according to claim 13, and an effective amount of a bioactive agent.

16. The pharmaceutical composition according to claim 15, wherein the bioactive agent is within the range from 0.01% to 50% by weight.

17. The pharmaceutical composition according to claim 15, wherein the bioactive agent is a protein or a peptide.

18. The pharmaceutical composition according to claim 17, wherein the protein or peptide is in its natural form or is modified by a polymer.

19. The pharmaceutical composition according to claim 17, wherein the protein is selected from the group consisting of growth hormone (GH), interferon (IFN), granulocyte colony stimulation factor (G-CSF), granulocyte macrophage colony stimulating factor(GMCSF), erythropoietin (EPO), interleukin (IL), fibroblast growth factor, follicle stimulating hormone (ESH), macrophage colony stimulating factor(M-CSF), nerve growth factor (NGF), octreotide, insulin, insulin-like growth factor(IGF), calcitonin, tumor necrosis factor (TNF), vascular endothelial growth factor (VEGF), epidermal growth factor (EGE), platelet-derived growth factor (PDGF), bone morphogenetic protein (BMP), tissue plasminogen activator (TPA), thrombopoietin(TPO), tissue growth factor and tumor necrosis factor(TNF).

20. The pharmaceutical composition according to claim 15, wherein the composition is in a form selected from the group consisting of gels, microspheres, nanoparticles, stripes, rods and films.

21. The pharmaceutical composition according to claim 15, wherein the composition is an aqueous solution of the multi-block copolymer in a concentration of 0.5 to 50% by weight.

22. The pharmaceutical composition according to claim 15, wherein the composition further comprises at least one member selected from the group consisting of PEG, hyaluronic acid, dextran, gelatin, collagen, chitosan, poloxamer 407, poloxamer 188, methylcellulose (MC), ethylcellulose (EC), hydroxyethylcellulose (HEC), methylhydroxyethylcellulose (MHEC), hydroxymethylcellulose, hydroxypropylmethylcellulose (H PMC) and hydroxypropylcellulose.

23. A method for a preparing the multi-block copolymer according to claim 6, having terminal carboxylic ends comprising:
1) preparing a reaction solution containing PEO—Y—PEO, slowly adding 0.5 to 1.0 equivalents of dicarboxylic acid dihalide based on 1 equivalent of the terminal end hydroxyl groups of the PEO—Y—PEO to the reaction solution and allowing the reaction to proceed;
2) adding more than 1 equivalent of additional dicarboxylic acid dihalide based on an equivalent of hydroxyl groups of the PEO—Y—PEO terminal end to the reaction solution to react until the reaction is completed;
3) precipitating the produced multi-block copolymer in an ether or hexane solvent and then dissolving the precipitate in alcohol; and
4) slowly adding ether or hexane so that a volume ratio of alcohol/ether or hexane is 1/1 to 1/20 to precipitate the multi-block copolymer.

24. A method for preparing a multi-block copolymer according to claim 6, which has metal carboxylate salts at both terminal ends of the multi-block copolymer comprising:
1) dissolving a multi-block copolymer in a solvent capable of being mixed with water, and
2) neutralizing the multi-block solution with sodium carbonate, sodium bicarbonate, calcium chloride, zinc chloride, magnesium chloride, iron chloride, copper chloride, silver nitrate, potassium chloride, or lithium chlorides
wherein the the multi-block copolymer of step 1) is prepared by:
preparing a reaction solution containing PEO—Y—PEO, slowly adding 0.5 to 1.0 equivalents of dicarboxylic acid dihalide based on 1 equivalent of the terminal end hydroxyl groups of the PEO—Y—PEO to the reaction solution and allowing the reaction to proceed;
adding more than 1 equivalent of additional dicarboxlic acid dihalide based on an equivalent of hydroxyl groups of the PEO—Y—PEO terminal end to the reaction solution to react until the reaction is completed;
precipitating the produced multi-block copolymer in an ether or hexane solvent and then dissolving the precipitate in alcohol; and
slowly adding ether or hexane so that a volume ratio of alcohol/ether or hexane is 1/1 to 1/20 to precipitate the multi-block copolymer.

25. A method for preparing the multiblock copolymer according to claim 6, having a sulfuric acid, phosphoric acid, or metal salt thereof at its polymer terminal end, comprising:
1) dissolving a multi-block copolymer in a solvent and reacting the solution with a sulfate trioxide pyridine complex, $C_5H_5NSO_3$, or a phosphorous oxychloride, $POCl_3$; and
2) optionally neutralizing the reaction mixture with sodium carbonate, sodium bicarbonate calcium chloride, zinc chloride, magnesium chloride, iron chloride, copper chloride, silver nitrate, potassium chloride, or lithium chloride to prepare a multi-block copolymer having a metal salt at its polymer terminal end,
wherein the the multi-block copolymer of step 1) is prepared by:
preparing a reaction solution containing PEO—Y—PEO, slowly adding 0.5 to 1.0 equivalents of dicarboxylic acid dihalide based on 1 equivalent of terminal end hydroxyl groups of the PEO—Y—PEO to the reaction solution and allowing the reaction to proceed;
adding an additional 0.1 equivalents of PEO—Y—PEO to the above reaction solution to react until the reaction is completed;
precipitating the produced multi-block copolymer in an ether or hexane solvent and then dissolving the precipate in alcohol; and
slowly adding ether or hexane so that the volume ratio of alcohol/ether or hexane is 1/1 to 1/20 to precipitate the multi-block copolymer.

26. The method according to claim 23, wherein PEO—Y—PEO is a poloxamer.

27. The method according to claim 23, wherein PEO—Y—PEO is purified by dissolving it in methylenechloride followed by precipitation in hexane, or separating it by layer-separation in an n—propanol/$H_2O$ solvent.

* * * * *